US009277853B2

(12) United States Patent
Nahen et al.

(10) Patent No.: US 9,277,853 B2
(45) Date of Patent: Mar. 8, 2016

(54) ENDOSCOPE AND OPTICAL FIBER ASSEMBLY

(75) Inventors: Kester Nahen, Heidelberg (DE); Ken Arnold, Soquel, CA (US); Steven Yihlih Peng, Elk Grove, CA (US); James Raymond Kermode, Los Altos, CA (US)

(73) Assignee: AMS Research, LLC, Minnetonka, MN (US)

( * ) Notice: Subject to any disclaimer, the term of this patent is extended or adjusted under 35 U.S.C. 154(b) by 2218 days.

(21) Appl. No.: 11/750,957

(22) Filed: May 18, 2007

(65) Prior Publication Data

US 2007/0270788 A1 Nov. 22, 2007

Related U.S. Application Data

(60) Provisional application No. 60/747,780, filed on May 19, 2006.

(51) Int. Cl.
*A61N 5/06* (2006.01)
*A61B 1/018* (2006.01)
*A61B 1/015* (2006.01)
(Continued)

(52) U.S. Cl.
CPC .................. *A61B 1/018* (2013.01); *A61B 1/015* (2013.01); *A61B 1/07* (2013.01); *A61B 18/24* (2013.01); *A61B 1/0017* (2013.01);
(Continued)

(58) Field of Classification Search
CPC .............. A61B 1/015; A61B 18/1492; A61B 2217/007; A61B 18/22; A61B 1/0615; A61B 2218/002

USPC ...................... 606/2–19; 607/88–94
See application file for complete search history.

(56) References Cited

U.S. PATENT DOCUMENTS 5,186,714 A    2/1993  Boudreault et al.
5,437,660 A    8/1995  Johnson et al.
(Continued)

FOREIGN PATENT DOCUMENTS

DE       4236329 A1    5/1994
DE       20218310 U1   2/2003
(Continued)

OTHER PUBLICATIONS

AU Examiner's First Report from corresponding AU Patent Application No. 2011200594; Oct. 17, 2011; 2 pgs.
(Continued)

*Primary Examiner* — Aaron Roane
(74) *Attorney, Agent, or Firm* — Bookoff McAndrews, PLLC

(57) ABSTRACT

An endoscope for an optical fiber provides for inflow and outflow of irrigant. A telescope is included having a field of view directed into a working region. The endoscope defines a "hooded region" with an extended, blunt tip. The optical fiber fits within the endoscope has a side or end firing tip with an emission surface. A guide element is adapted to movably support the optical fiber in a position spaced away from the working region, and limit lateral movement of the tip without preventing longitudinal and rotational movement. An irrigant flow arrangement operates to direct inflowing irrigant over the emission surface of the tip. The fiber is assembled with a fiber coupler, a handle, a fiber port cap, and a travel limiter fixed to the fiber at a predetermined distance from the tip. The travel limiter cooperates with the endoscope and the fiber port cap to limit longitudinal and rotational movement of the fiber.

21 Claims, 13 Drawing Sheets

(51) Int. Cl.
*A61B 1/07* (2006.01)
*A61B 18/24* (2006.01)
*A61B 18/22* (2006.01)
*A61B 19/00* (2006.01)
*A61B 1/00* (2006.01)

(52) U.S. Cl.
CPC .. *A61B 2018/2272* (2013.01); *A61B 2019/304* (2013.01); *A61B 2019/305* (2013.01)

(56) References Cited

U.S. PATENT DOCUMENTS

| | | | |
|---|---|---|---|
| 5,593,404 | A | 1/1997 | Costello et al. |
| 5,649,924 | A | 7/1997 | Everett et al. |
| 5,672,171 | A * | 9/1997 | Andrus et al. ............ 606/15 |
| 5,944,654 | A | 8/1999 | Crawford |
| 6,282,442 | B1 | 8/2001 | DeStefano et al. |
| 6,454,762 | B1 | 9/2002 | Rosler et al. |
| 6,699,184 | B2 | 3/2004 | Felix et al. |
| 6,712,757 | B2 | 3/2004 | Becker et al. |
| 6,802,838 | B2 | 10/2004 | Loeb et al. |
| 7,344,528 | B1 * | 3/2008 | Tu et al. .................. 606/7 |
| 2003/0060813 | A1 * | 3/2003 | Loeb et al. ............... 606/17 |
| 2005/0132399 | A1 | 6/2005 | Smith |
| 2005/0177101 | A1 | 8/2005 | Wilson |
| 2005/0177145 | A1 | 8/2005 | Nahen et al. |
| 2006/0084959 | A1 * | 4/2006 | Davenport et al. ......... 606/15 |

FOREIGN PATENT DOCUMENTS

| | | |
|---|---|---|
| JP | 10243946 | 9/1998 |
| WO | 9320742 A1 | 10/1993 |

OTHER PUBLICATIONS

International Search Report for PCT Application PCT/US07/69310 mailed on Jan. 29, 2008.
Requisition by the Examiner from corresponding CA Patent Application No. 2,802,925; Jan. 6, 2015; 4 pgs.

* cited by examiner

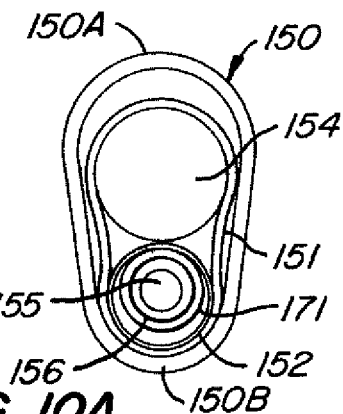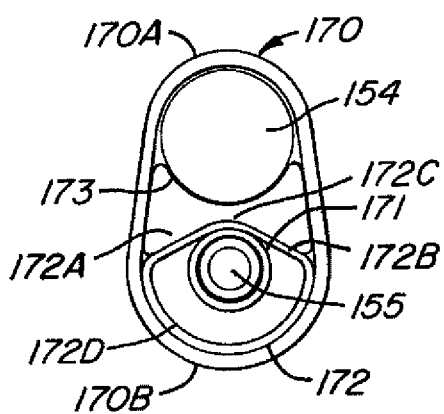
FIG. 10A
FIG. 11A
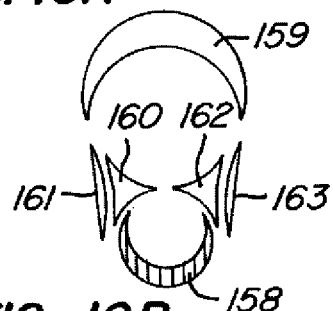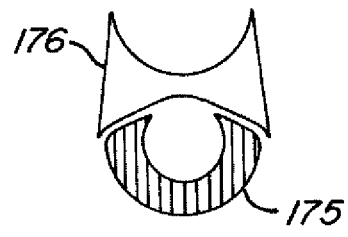
FIG. 10B
FIG. 11B
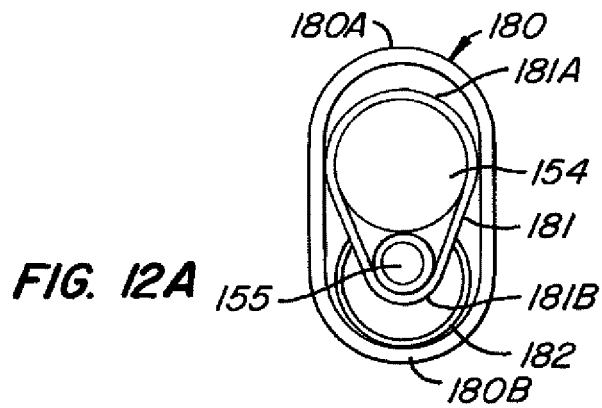
FIG. 12A
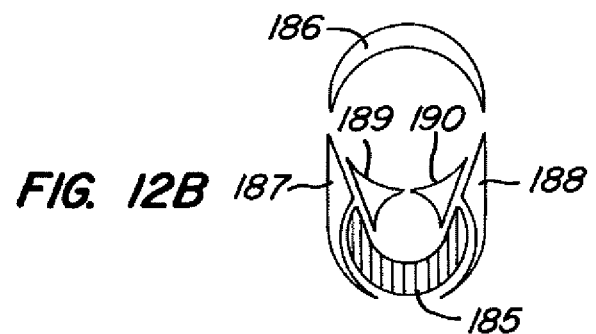
FIG. 12B

ENDOSCOPE AND OPTICAL FIBER ASSEMBLY

CROSS-REFERENCE TO RELATED APPLICATIONS

This application claims the benefit of, and incorporates by reference, U.S. Provisional Application No. 60/747,780, filed 19 May 2006.

BACKGROUND OF THE INVENTION

1. Field of the Invention

The present invention relates generally to endoscopes, and in particular the configuration of a handle used for a multi-function endoscope.

2. Description of Related Art

An endoscope is an illuminated medical device used look inside the body and examine organs. An endoscope can be rigid or flexible. Endoscopes designed for particular procedures often have specialized names, such as cystoscope (urethra, bladder), nephroscope (kidney), bronchoscope (bronchi), laryngoscope (larynx), otoscope (ear), arthroscope (joint) and laparoscope (abdomen). In addition to being used for viewing and examination, endoscopes are often used with various types of medical instruments for diagnostic and therapeutic procedures. An example of these medical instruments includes a medical laser device using fiber optics to deliver the laser energy to, typically, the distal end of the endoscope. Other medical instruments that can be used with endoscopes include grasping, cutting, tissue sampling and suturing medical instruments as well as medical instruments designed to provide energy other than laser energy such as RE and ultrasonic energy.

Endoscopic removal of tissue by means of lasers has been realized in procedures such as photoselective vaporization of prostate (PVP) for the treatment of lower urinary tract symptoms (LUTS) due to benign prostatic hyperplasia (BPH). Lasers in the visible and invisible spectral range have been utilized for endoscopic procedure of tissue removal. Tissue removal is typically carried out under endoscopic visualization of the operating field through a telescope. Laser light is guided to the operating field by an optical light guide (laser fiber). To steer the light guide to the target tissue an endoscope is often utilized. In some implementations the telescope can be embodied in the endoscope as a fixed or modular component. Also, such procedures rely on a supply of irrigating fluid to the operating region, to remove debris, cool tissue and otherwise cooperate with the activity.

Performing a surgical laser procedure through an endoscope creates several challenges. Vaporization of tissue in a body cavity filled with an irrigant can create vapor bubbles and tissue particles that get released into the irrigant and that can obscure the view of the surgeon.

Controlling the surgical effect the laser has on tissue requires the surgeon to position the laser fiber with high precision. The surgeon has to consider the characteristics of the laser beam such as its divergence coming out of the laser fiber and control the distance between laser fiber and tissue to achieve the desired effect. In some instances the laser effect can change its nature dependent on the distance between laser fiber and tissue. In some cases vaporization will occur when the fiber is close to tissue but coagulation without vaporization will occur when the fiber is further away from tissue.

The surgeon has to control the position of the distal tip of the laser fiber relative the distal tip of the endoscope to avoid damage to the endoscope by unintentional exposure of the endoscope to laser light.

Thus, in some high power laser applications, it is possible to damage an endoscope by inadvertently directing laser radiation into the structure. In addition, it is necessary to provide for an effective irrigation flow in such systems. Finally, is desirable to provide a structural design, which is comfortable to hold and utilize by surgeons. An endoscope is described herein that allows surgeons to safely and effectively perform laser surgery, including transurethral laser vaporization of prostate tissue.

SUMMARY

An endoscope and an optical fiber assembly adapted for use with endoscopes are described. An endoscope described herein is adapted for insertion within a body lumen, and comprises an external cannula having a proximal end and a distal end, and a plurality of tubes within the external cannula. Tubes in the plurality of tubes have respective ends at or near the distal end of the external cannula and are adapted for receiving a telescope and optical fiber and for providing inflow and outflow of irrigant. A telescope is included having a field of view directed into the working region at or near the distal end. The distal end of the external cannula has a bottom side and a top side, arranged to define a "hooded region" with an opening facing the bottom side opening a working region within the body lumen and with an extended, blunt tip serving to allow insertion into the body lumen, and provide an open volume within the body lumen to receive the optical fiber tip and allow direct visualization in the working region during operation.

An optical fiber assembly is described that fits within the endoscope, having a fiber end element, such as a side firing tip, with an emission surface through which radiation from the optical fiber is directed into the working region. The endoscope and optical fiber assembly cooperate to maintain the tip of the fiber spaced away from the tissue in the working region by a desired amount to assist management of the energy density delivered to the working region, while preventing the laser energy from being directed away from the working region, particularly to prevent directing laser energy onto the endoscope. A guide element at or near the distal end of the external cannula is adapted to movably support the optical fiber in a position spaced away from the inner wall of the external cannula. Also, the guide element limits lateral movement of the tip without preventing longitudinal movement of the tip within the working region. Also, the guide element does not prevent rotational movement of the tip over at least the predetermined arc.

An irrigant nozzle element at the end of one of the plurality of tubes at or near the distal end of the external cannula is provided. The irrigant nozzle element having a crescent shaped opening in an implementation described herein at the distal end below the guide element for the optical fiber, is arranged to direct inflowing irrigant over the emission surface of the tip as the tip is moved over a predetermined distance longitudinally into the working region, and as the tip is moved rotationally through the predetermined arc. Also, an irrigant back flow port is included at the distal end which withdraws irrigant from the working region in cooperation with the irrigant nozzle element so that the flow of irrigant over the emission surface of the tip is maintained.

An optical fiber assembly adapted to work with the endoscope includes an optical fiber as mentioned above having a tip at or near the distal end of the optical fiber. The tip has an emission surface through which radiation from the optical fiber is directed. A fiber port cap, such as a resilient sealing element, is included. The cap has a fiber receiving opening and is adapted to cooperate with and at least partially close a corresponding fiber port on the proximal end of the endoscope. A travel limiter is coupled to the optical fiber at a predetermined distance from the tip of the optical fiber between the fiber port cap and the tip. The travel limiter is adapted to cooperate with a corresponding element in the endoscope, such as a cylindrical bearing surface with a stop element extending into the cylinder, to limit rotational movement of the optical fiber relative to the endoscope to a predetermined arc, and to limit longitudinal movement of the optical fiber relative to the endoscope. In embodiments described herein, the fiber port cap is adapted to act as a stop, in cooperation with the travel limiter and the cylindrical bearing surface in the fiber port, for longitudinal movement of the optical fiber, preventing movement of the emission surface that would withdraw it into the endoscope.

A fiber coupler is mounted at the proximal end of the optical fiber assembly in embodiments described herein, adapted to couple the optical fiber to a laser system. Also, a handle or knob is secured on the optical fiber assembly, preferably a predetermined distance away from the travel limiter with the fiber port in between, which is adapted to be gripped for the purposes of manipulating the optical fiber for longitudinal and rotational movement during use.

Other aspects and advantages of the technology described herein are set forth in the drawings, the detailed description and the claims which follow.

BRIEF DESCRIPTION OF THE DRAWINGS

FIGS. 10A and 10B illustrate a first configuration of the walls of the external cannula and internal structure for an embodiment of the endoscope, and a corresponding inflow and outflow pattern.

FIGS. 11A and 11B illustrate a second configuration of the walls of the external cannula and internal structure for an embodiment of the endoscope, and a corresponding inflow and outflow pattern.

FIGS. 12A and 12B illustrate a first configuration of the walls of the external cannula and internal structure for an embodiment of the endoscope, and a corresponding inflow and outflow pattern.

DETAILED DESCRIPTION

A detailed description of embodiments of the present invention is provided with reference to the FIGS. 1-19.

Figure 1:
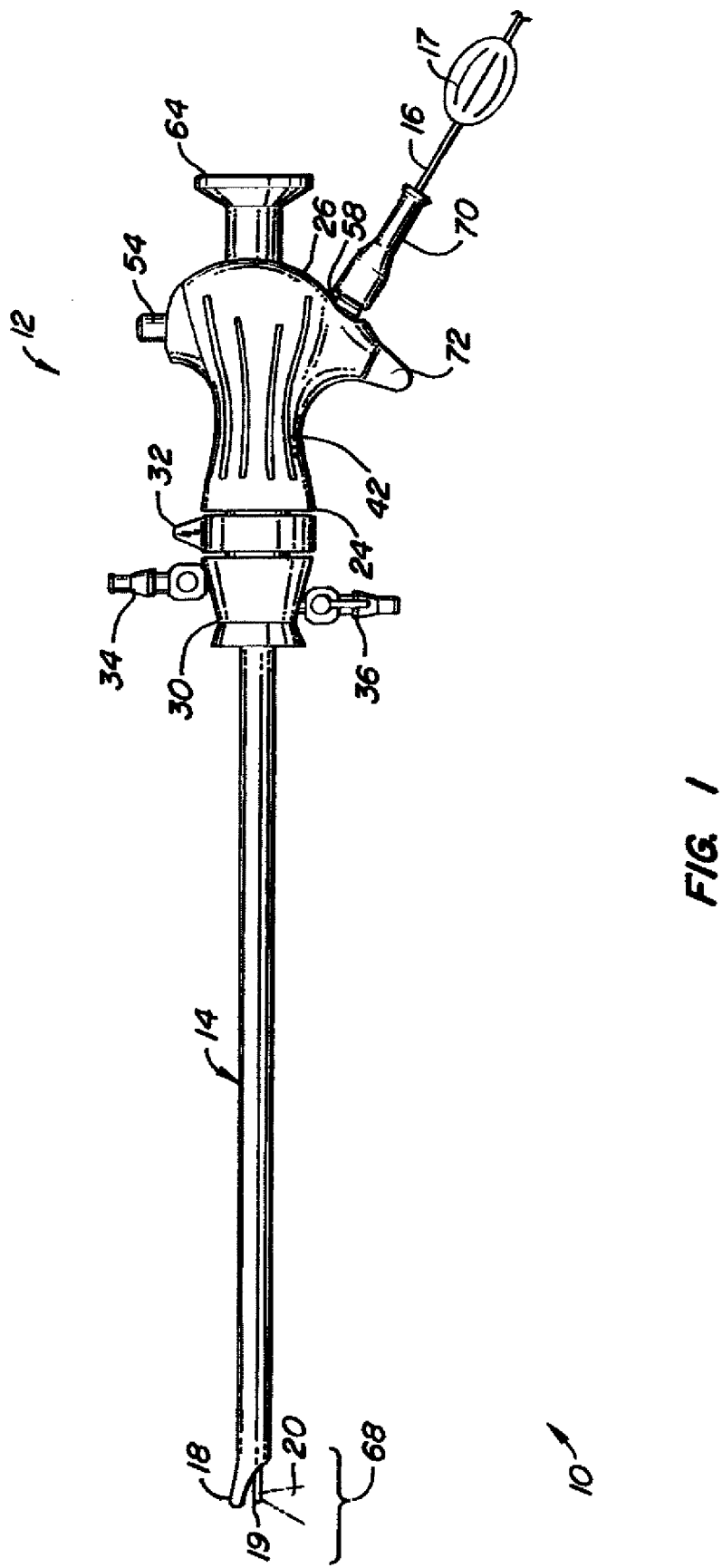
FIG. 1 is a simplified overall view of a multifunction endoscope including a handle made according to the invention.

FIG. 1 illustrates a multifunction endoscope 10, such as a transurethral cystoscope, including a handle 12 with an external cannula 14 extending distally from the handle 12. In this embodiment the multifunction endoscope 10 is designed for use with a medical laser device of the type including an optical fiber 16 having a fiber end member 19 which extends into a cavity formed by a hood structure (described in more detail below) on the distal tip 18 of external cannula 14. The optical fiber 16 has a knob 17 attached near the handle 12 that is adapted to be used by a surgeon to manipulate the position of the fiber end member, rotationally and longitudinally. External cannula 14 has a number of passageways or lumens formed by an internal structure, not shown, extending generally from handle 12 to distal tip 18 to accommodate, in this disclosed embodiment, optical fiber 16 and fiber end member 19, a telescope type of visualization device typically coupled to a display monitor (not shown), an inflow irrigation pathway, and an outflow or suction pathway. The endoscope 10 in the illustrated embodiment includes an internal cannula, which receives the fiber 16 in a manner, which allows easy movement of the fiber 16 at least over a range of motion that allows manipulation of the fiber end member 19 longitudinally and rotationally within a working field by a surgeon grasping the knob 17. Other embodiments are adapted for manipulation of the fiber end member 19 by a mechanical system under computer control with active feedback based on the video images of the procedure, with or without real time user input.

Individual lumens may be used for a single purpose, such as delivery of irrigation liquid, or for two or more purposes, such as housing the telescope and an optical fiber.

As suggested in FIG. 1, a laser beam 20 is directed laterally in the illustrated embodiment from laser end element 19 in a side-firing fashion. Optical fiber 16 could also have an end element adapted for forward firing. A telescope provides visualization in the general direction of laser beam 20 with appropriately angled optical elements at its distal end. In addition, other types of medical instruments may be used as a part of endoscope 10 instead of, or in addition to, a medical laser device.

Figure 1A:
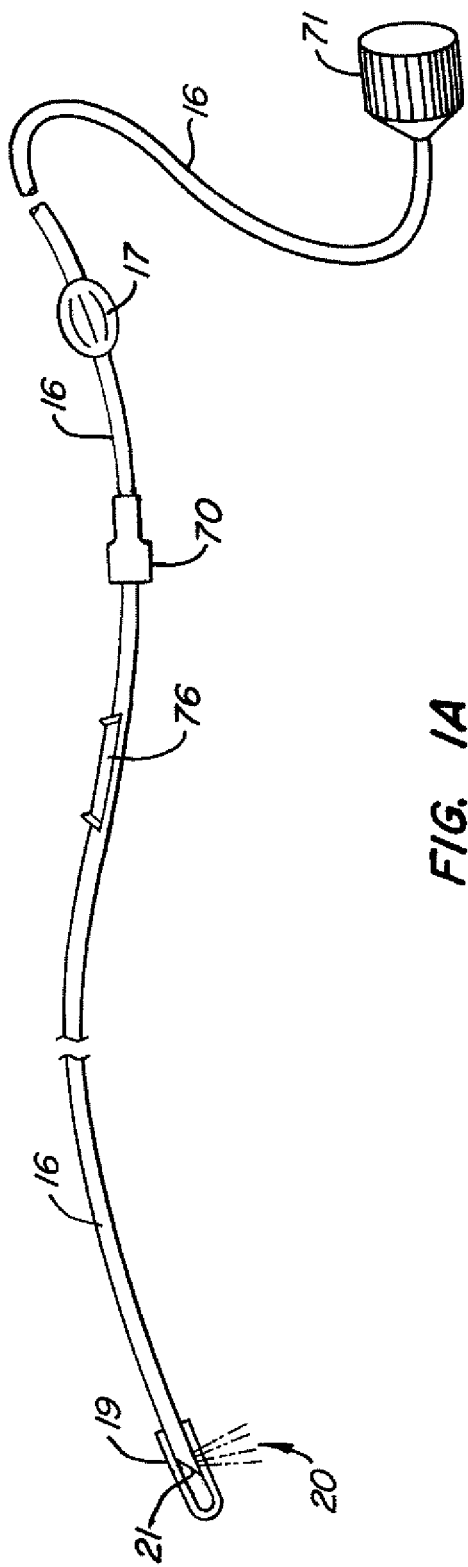
FIG. 1A is a simplified side view of a portion of laser fiber showing a rotation limiting element, a coupler and a fiber manipulator mounted thereto.

FIG. 1A is a simplified diagram of an optical fiber assembly adapted for use with the endoscopes as described herein. The fiber 16 is connected to a coupler 71 adapted to connect the fiber to the output of a laser system. The fiber end element 19 in the illustrate embodiment comprises a fused quartz cap which captures air between a beveled end 21 of the fiber 19. The air/fiber interface provided by the beveled end 21 causes essentially total internal reflection of the beam 20 in the side firing direction. At a predetermined distance from the fiber end element 19, a travel limiter 76, in the form of a cam in this embodiment, is attached to the fiber 16. The travel limiter 76 is adapted to cooperate with a corresponding element within the endoscope, as described in more detail below, to prevent the surgeon from withdrawing the fiber end element 19 into the cannula so that the beam 20 does not damage the cannula, and to prevent the surgeon from rotating the fiber end element 19 toward the hood structure on the distal tip 18 of the external cannula, so that the beam 20 does not damage the hood structure on the distal tip 18. In addition, the fiber is threaded through a fiber port cap 70, which is adapted to couple with a fiber port on the endoscope 10, as illustrated in FIG. 1, which secures the travel limiter 76 within the endoscope, and provides a seal on the cannula within which the fiber 16 is received without interfering with movement of the fiber within the predetermined ranges of longitudinal and rotational motion. The fiber port cap is preferably a flexible material having an elastic opening adapted to receive the fiber, and a lip adapted to fit over a corresponding ridge on the fiber port, at least partially closing, and in a preferred embodiment substantially sealing, the fiber port to prevent fluid leakage while allowing for longitudinal and rotational movement of the fiber.

In a preferred embodiment the longitudinal motion of optical fiber 16 is directed axially along axis 28 (illustrated in FIG. 2) and also rotationally about its own axis to permit laser beam 20 to be directed proximally and distally as optical fiber 16 moves generally along axis 28 as well as being swept side to side as optical fiber 16 rotates about its own axis. Distal tip 18 of external cannula 14 is beveled to permit this range of movement of laser beam 20 while providing for proper viewing of working region 68.

Figure 2:
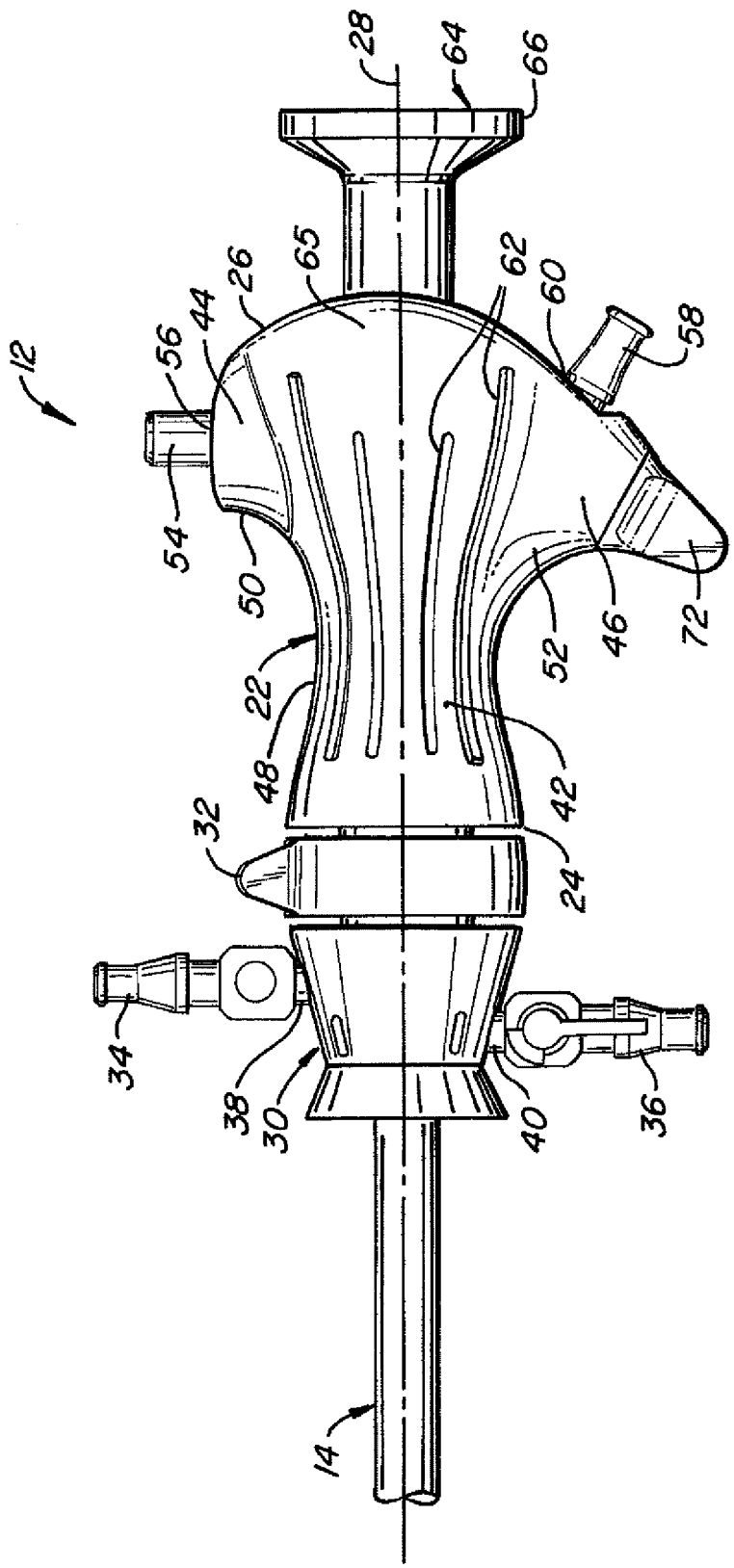
FIG. 2 is an enlarged view of the handle of FIG. 1.

FIG. 2 shows more detail of handle 12. Handle 12 includes a body cover portion or cover 22 having a distal end 24 and a proximal end 26 and defining a central axis 28. The axial distance between distal and proximal ends 24, 26 is preferably about 8 to 15 cm, and typically about 9 to 12 cm. This size range is chosen primarily to accommodate different hand grasping techniques, such as shown in FIGS. 3-6 for users with a range of sizes of hands and styles of use for the endoscope. Handle 12 also includes a supplemental body cover 30 positioned distally of body cover 22 with a coupler 32 therebetween adapted for covering the proximal end of the external cannula 14 and various fittings used for connecting the internal structures to the external cannula 14. The external cannula 14 is connected with irrigation inflow and outflow fittings 34, 36, and secured by bayonet mount 32 to internal structures (not shown), which are adapted to receive the telescope 64 and the fiber 16. Handle 12 has a number of ports opening into the interior of the handle. For example, inflow and outflow fittings 34, 36 extend from supplemental body cover 30 and provide access to inflow and outflow ports 38, 40 which open into an inflow irrigation pathway defined by internal structures and an outflow or suction pathway extending along external cannula 14. Inflow fitting 34 may be connected to a source of an appropriate irrigation liquid, such as saline fed by a gravity feed structure or by a pump, while outflow fitting 36 may be connected to an appropriate suction source.

Body cover 22 has a smoothly tapering outer surface 48 that tapers radially inwardly from distal and proximal ends 24, 26 towards a central or waist portion 42. The circumference of proximal end of 26 is larger than the circumference of distal end 24, which is larger than the circumference of waist portion 42. Outer surface 48 has a generally circular, slightly oval cross-sectional shape along axis 28 with a diameter in a range of about 1.5 to 2 cm, for example. Outer surface 48 may have other, preferably smoothly curving shapes, such as oval and egg-shaped, at various positions along axis 28 or along the entire length of axis 28.

Handle 12 also has first and second body cover extensions 44, 46 extending radially outwardly from the outer surface 48 of body cover 22 adapted to comfortably shield the surgeon's hand from fittings for the telescope and the fiber 16. Extensions 44, 46 are positioned between proximal end 26 and waist portion 42. Extensions 44, 46 have smoothly curving, distally-facing outer surfaces 50, 52 to provide a smooth transition between outer surface of 48 of body cover 22 and extensions 44, 46. As seen in FIG. 2, first body cover extension 44 extends generally directly radially outwardly while the second body cover extension 46 extends both radially outwardly and distally. An illumination fitting 54 extends from first body cover extension 44 and opens into an illumination port 56, discussed below. An optical fiber fitting 58 extends from second body cover extension 46 and opens into an optical fiber port 60. Optical fiber 16 passes through fitting 58, through port 60, and through an appropriate passageway in handle 12 for entry into and through an appropriate lumen within external cannula 14. A valve handle 72 is mounted flush with second body cover extension 46 with a smooth or otherwise comfortable surface transition. The valve handle 72 is turned to control a stop cock within the handle 12, to seal off port 60 when desired, typically when laser fiber 16 is removed from handle 12.

As shown in FIG. 2, smoothly tapering outer surface 48 is provided with a number of grooves 62 to facilitate grasping by the user. The same or other types of embossing or debossing may also be provided for outer surface 48 as well as outer surfaces 50, 52 to promote a good grip of handle 12. One or more of outer surfaces 48, 50 and 52 may be provided with a mat or other suitable surface texture. In the preferred embodiment body cover 22 is of a stiff polymer material or metal. In alternative embodiments, the entire body cover 22, portions of body cover 22 and/or a skin on the body cover 22 may comprise a resilient or otherwise yieldable elastomer material.

Endoscope 10 also includes a telescope 64 extending through a telescope port 65 at proximal end of 26 and aligned with axis 28. Telescope 64 includes a camera fitting 66 to permit images of the working region 68 in the vicinity of laser beam 20 captured by the telescope at distal tip 18 to be recorded and/or monitored during use. Illumination port 56 is coupled to the interior of telescope 64 so the light from the illumination source passes distally along the telescope to illuminate working region 68.

A simple endoscope used for examination of an organ may have only two ports, one for the light source and one for the optical image. However, endoscopes used for medical procedures such as ablation of tissue using laser energy will typically have many more ports and therefore make the design of the proximal portion of the endoscope more complicated. The increased complexity includes the presence of tubes, lines, wires and other things extending from the proximal portion of the endoscope. One aspect of the endoscope is based on the recognition that different individuals using the same endoscope will often hold and manipulate the endoscope by its proximal portion in different ways. This is particularly true for multifunction endoscopes used for both of viewing and for treatment, at least in part because of the increased complexity of the procedure and the number of things extending from the proximal portion, as well as the personal preferences of the operator.

The handle described herein for a multifunction endoscope comprises a body cover, a first body cover extension and a second body cover extension. The body cover comprises distal and proximal ends with an axis extending therebetween with a waist between the distal and proximal ends. The distal and proximal ends and the waist have distal and proximal circumferences and a waist circumference, respectively. The proximal circumference is larger than the waist circumference and the distal circumference is larger than the waist circumference. The body cover also comprises an outer surface, the outer surface tapering from the distal end to the waist and from the proximal end to the waist. The first body cover extension extends in a first radial direction from the outer surface of the body cover between the proximal end and the waist. The second body cover extension extends in a second radial direction from the outer surface of the body cover between the proximal end and the waist.

In some embodiments the proximal circumference is larger than the distal circumference. The outer surface is preferably a smoothly tapering outer surface. The body cover may comprise a plurality of ports at a proximal portion thereof. The handle may also comprise a second body cover positioned distally of the distal end of the body cover. The second body cover may comprise additional ports therein.

Figure 3:
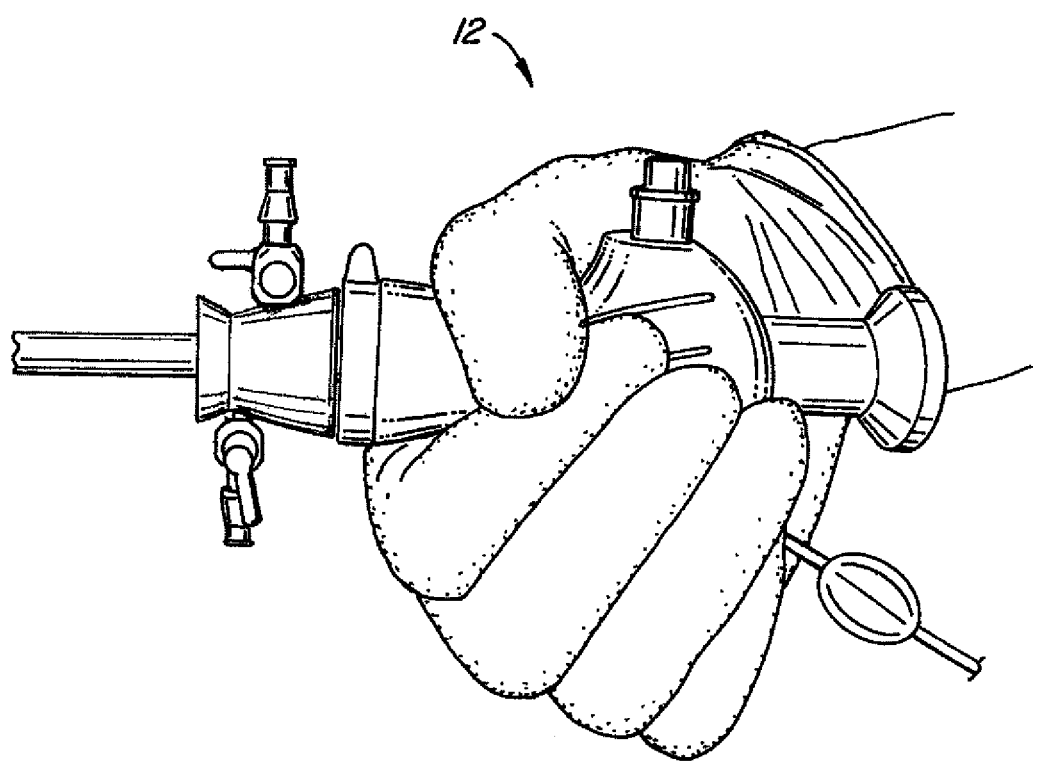
FIGS. 3-6 illustrate four different handle holding techniques accommodated by the handle of FIGS. 1 and 2.
Figure 4:
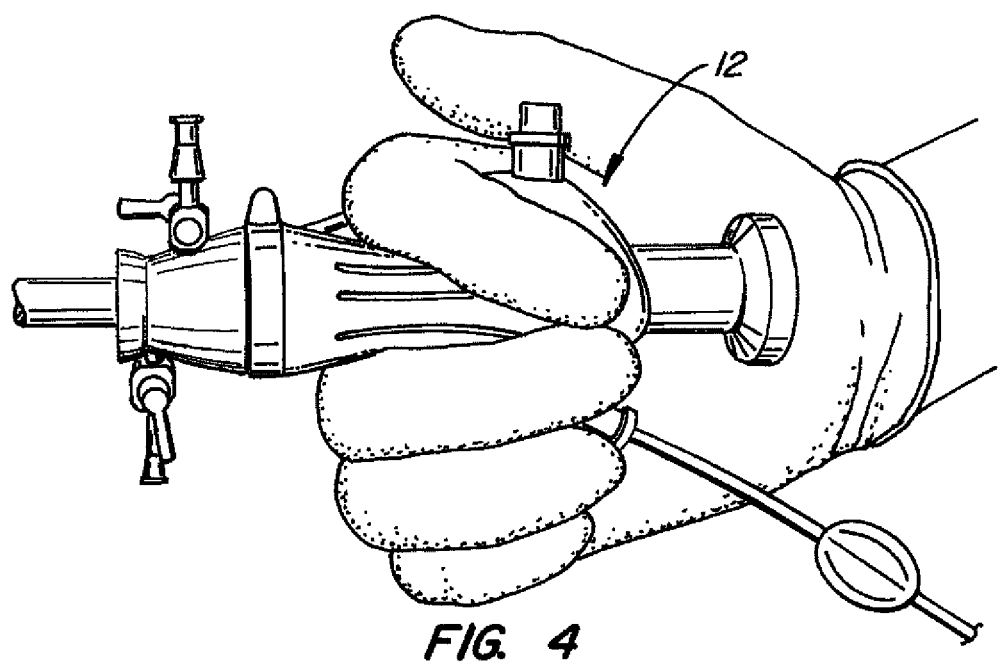
Figure 5:
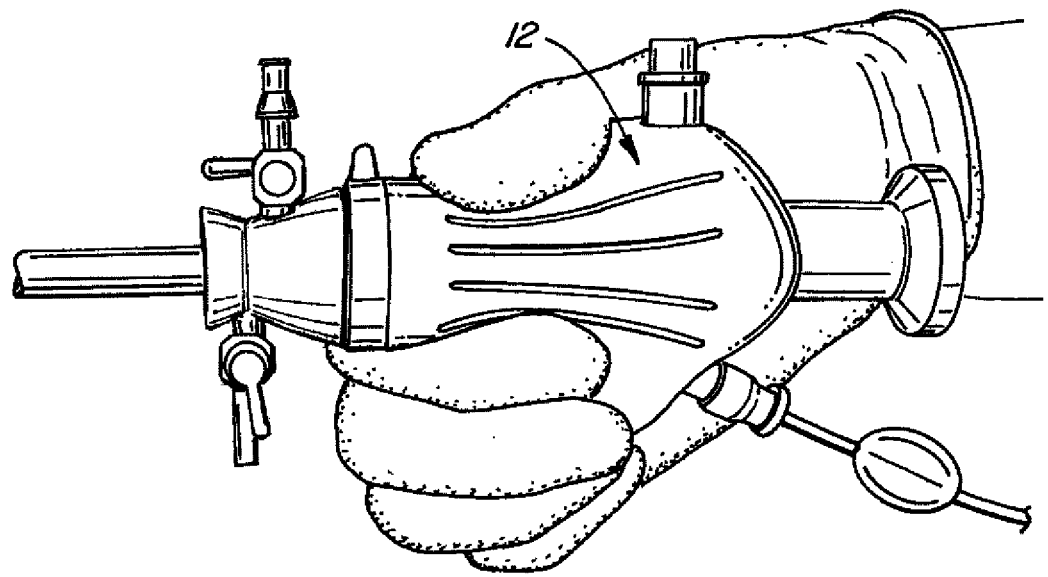
Figure 6:
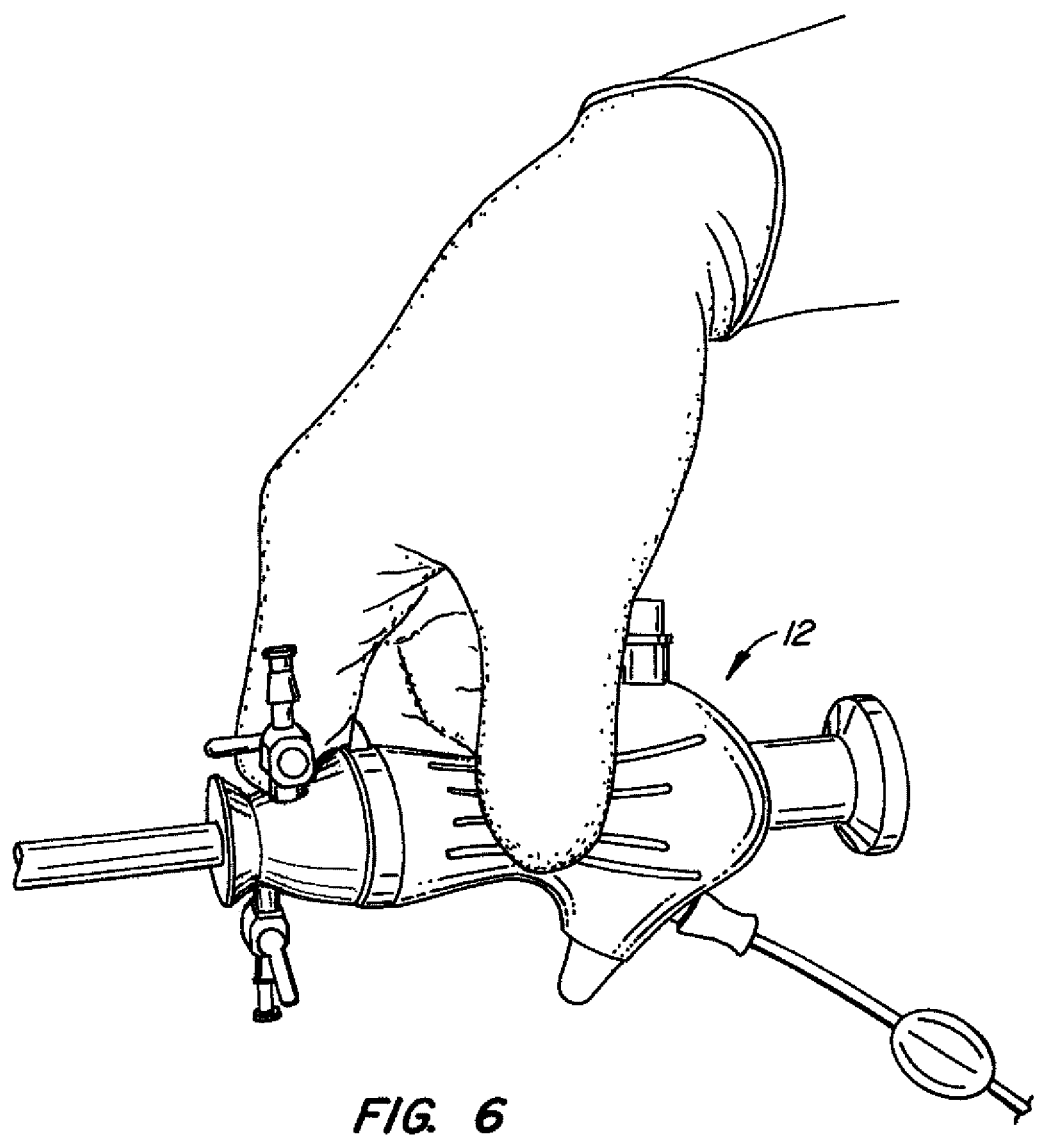

FIGS. 3-6 illustrate four typical ways a surgeon can comfortably and securely hold or grasp handle 12 of endoscope 10 by grasping body cover 22 with one hand while leaving the other hand free to manipulate laser fiber 16 using fiber manipulator knob 70 to adjust both the axial and rotary positions of laser beam 20. The shape of handle 12 may accommodate other grasping techniques. The different grasping techniques can be based upon different personal preferences as well as the particular procedure being accomplished. For example, an operator may find the grasping technique of FIG. 6 to be most satisfactory when initially introducing the endoscope 10 to the target site to provide the most sensitivity to this procedure. The provision of the smaller circumference waist portion 42 provides an exceptionally secure grasping surface between the user's thumb and opposed fingers. The grasping techniques of FIGS. 3 and 4 provide extremely stable and secure positioning of handle 12 due to the provision of the smaller circumference waist portion 42 and the larger circumference proximal end 26, as well as first and second body cover extensions 44, 46 with their smoothly tapering, forward facing outer surfaces 50, 52. The grasping technique of FIG. 5 may be chosen by some users when, for example, manipulating laser fiber 16 extending from optical fiber fitting 58, In all cases, the smoothly tapering surfaces from the larger circumference distal and proximal ends 24, 26 to the smaller circumference waist portion 42 provide a comfortable and a secure gripping surface for the user.

Figure 7:
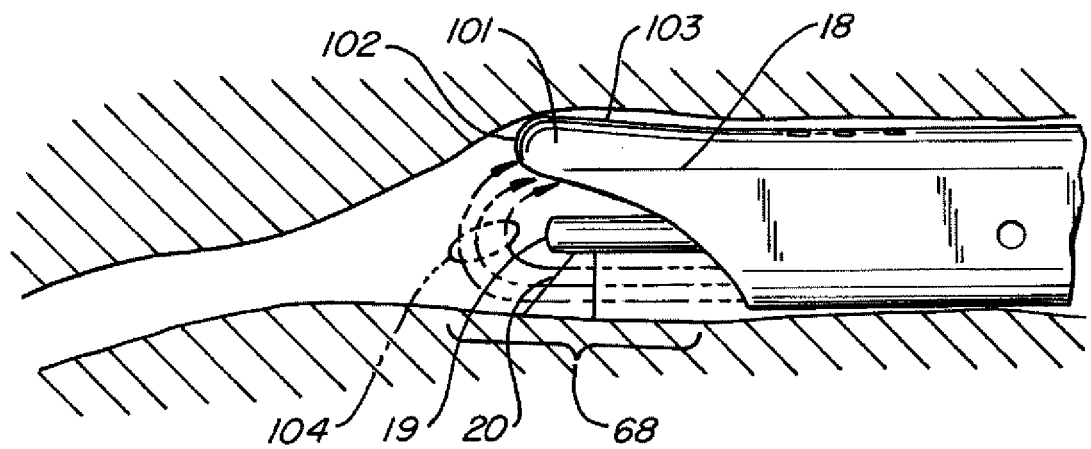
FIG. 7 is a side view of the distal end of the endoscope positioned within a urethra near prostate tissue.

FIG. 7 illustrates the distal end 18 of the endoscope positioned within a urethra adjacent prostate tissue. The fiber end element 19 directs radiation 20 into the prostate tissue to cause vaporization or other effects in the tissue. The distal end 18 includes a hood structure 101 with a blunt distal face 102 adapted to be inserted into the urethra. The hood structure 101 acts as an obturator, which prevents constriction of the urethra onto the fiber end element 19, and defines an open area between the top surface 103 and the working region 68 on the prostate tissue. The internal structure (not shown) within the external cannula at the distal end 18 includes a guide element that is adapted to movably support the optical fiber in a position so that the emission face of the end element 19 is spaced away from the working region 68 on the prostate tissue within the open area defined by the hood structure 101. In addition, the external cannula includes a nozzle for directing inflowing irrigant, and regions for suction of out flowing irrigant, which together define an irrigation pathway represented by arrows 104. The irrigation pathway 104 flows across the emission face of the fiber end element 19 as the fiber end element 19 is moved within the open area, maintaining irrigation flow during the delivery of radiation to facilitate clear visualization through the telescope and to maintain the emission face of the fiber end element 19 clear of debris.

Figure 8:
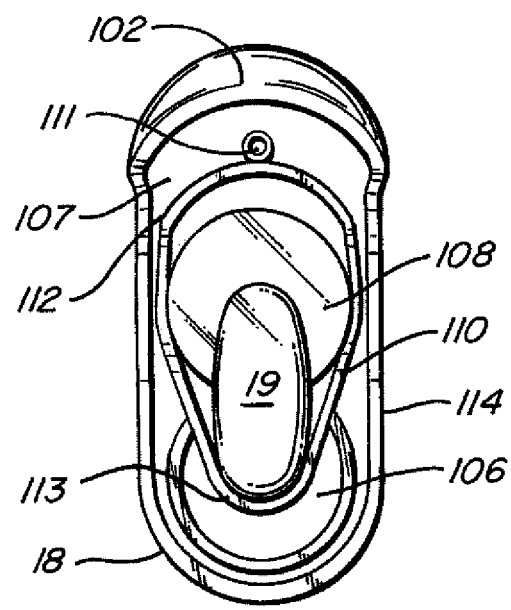
FIG. 8 is a prospective view of the opening at the distal end of the endoscope, looking from the working region into the opening.

FIG. 8 provides a prospective of the distal end of the endoscope outer cannula, taken from the direction of the working region 68 where the fiber end element 19 extends outwardly between the working region and the telescope face 108, partially blocking the telescope face 108 in this view. As illustrated in FIG. 8, the distal face 102 of the endoscope represents the end of a hood structure. An opening on the end of the external cannula is defined by the distal face 102, and side walls, which slope away from the end. The inner cannula 110 includes a first lumen having an upper ridge 112, which receives the telescope so that the telescope face 108, protruding slightly from the upper ridge 112 in this view, faces the working region 68. The inner cannula 110 also supports the fiber end element 19. Thus the upper ridge 112 has a radius, which matches that of the telescope, and the lower ridge 113 as a radius, which matches that of a bearing surface on the fiber end element 19. An irrigant inflow channel is defined by a second lumen which is bonded to the first lumen by welding or otherwise, and having crescent shaped opening 106 which acts as an irrigant nozzle directing irrigation flow outwardly over the fiber end element 19. In the illustrated embodiment, a tube 111 is attached to the outside surface of the upper ridge 112 of the first lumen acting as a spacer between the inner cannula that defines the first and second lumens, and of the inside wall at the top of the outer cannula. An opening 107 established by tube 111 between the inner cannula and the external cannula provides an irrigation outflow channel which is coupled to a suction source tending to cause the irrigant which is forced through the crescent shaped opening 106 of the irrigant inflow channel to flow outwardly and an upwardly across the fiber end element 19.

Figure 9:
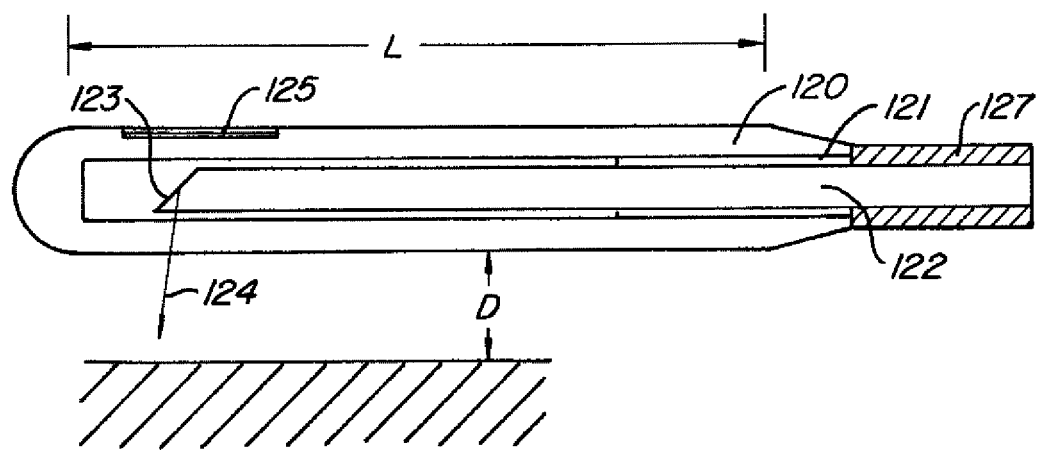
FIG. 9 is a diagram of a representative fiber end element for a side firing optical fiber.

FIG. 9 is a cross-sectional view of a representative fiber end element 19. The representative fiber end element 19 in FIG. 9 includes a fused quartz cap 120, which is attached by glue 121 or otherwise to the cladding 122 of an optical fiber. In a preferred embodiment, the optical fiber has a relatively large ratio of the diameters of the cladding and the core to reduce unwanted back scattering of the radiation, as described in U.S. Pat. No. 5,428,699, entitled "Probe having optical fiber for laterally directing laser beam" which is incorporated by reference. The optical fiber 122 has a beveled face 123. The cap 120 captures air in an area around the beveled face 123 to establish an air/fiber core interface at which substantially all of the radiation from the fiber is reflected on line 124 on to the tissue. The optical fiber cladding 122 is surrounded by a protective sheath 127 along the length of the fiber. The sheath 127 is removed within the cap, leaving the core and cladding. The quartz cap 120 is beveled near the fitting with the protective sheath 124. The cap 120 has a reflective coating 125 in a region adjacent the beveled face 123 to block or diffuse any back reflected radiation, preventing damage to the endoscope or to tissue that is not intended to be irradiated. As illustrated, the cap 120 has a length L over which it has a constant diameter and is circular in cross-section, so that it is adapted to fit against, and provide a bearing surface for, the lower ridge 113 of the first lumen described with reference to FIG. 8, over a range of longitudinal motion that is close to the length L. Also, as mentioned above, the endoscope includes a guide element, which positions the fiber end element 19 so that the emission face is spaced away from the target tissue. In FIG. 9, the dimension D (on the order of 1 to 2 mm for a transurethral cystoscope) represents the spacing provided by the guide element within the endoscope. This spacing operates to assist the surgeon to maintain a relatively constant distance between the emission face on the fiber end element 19, and the target tissue, and therefore improve consistency of the energy density on the tissue. Also, it operates to create a region within which the irrigation flow is readily accepted and directed over the emission face of the fiber end element 19 within the range of motion allowed by the device.

FIGS. 10A-10B, 11A-11B, and 12A-12B illustrate alternative configurations for the external cannula and internal structure of the endoscope. In FIG. 10A, the external cannula 150 has a larger radius at an arcuate top surface 150A than at a lower arcuate surface 150B and an essentially flat wall between the arcuate surfaces 150A, 150B. The internal structure includes an internal cannula 151 adapted to receive the telescope 154 and an irrigant inflow tube 152. The tube 152 is bonded to a tubular guide element 156, which receives the fiber end element 155. Inner cannula 151 has an arcuate top surface 151A adapted to match the radius of the telescope 154. Also, the inner cannula 151 has an arcuate bottom surface 151B adapted to match the radius of the tube 152, so that they are securely positioned within the cannula 151. The guide element 156 is bonded to the tube 152. In one embodiment, the end element 155 is bonded to the guide element 156, and both are movable as a unit together with the tube 152. In another embodiment, the end element 155 moves freely within the guide element 156. FIG. 10B illustrates the flow of irrigant for the embodiment illustrated in FIG. 10A. Irrigant inflow (hatched in the drawing) occurs in a region 158 having a crescent shape below and partially surrounding the fiber end element 155 as it is positioned as described above. Irrigant outflow (not hatched in the drawing) is primarily directed through the region 159 near the top of the external cannula, and additional irrigant flows through regions 160, 161, 162 and 163 as illustrated through the inner cannula and the outer cannula.

In FIG. 11A, the external cannula 170 has a smaller radius at the top surface 170A then at the lower surface 170B and an essentially flat wall between the arcuate top and bottom surfaces 170A, 170B. The internal structure includes a tubular guide 173 adapted to receive the telescope 154, and a crescent shaped irrigant inflow tube 172, with a top surface that comprises two essentially flat regions 172A, 172B that intersect in a smaller radius arcuate region 172C, and a bottom surface 172D that comprises an arcuate portion adapted to match the radius of the lower surface 170B of the external cannula. The smaller radius arcuate region 172C is adapted to match the radius of a guide element 171, which supports the fiber end element 155. The guide element 171 is bonded to the smaller arcuate region 172C. FIG. 11B illustrates the flow of irrigant for the embodiment illustrated in FIG. 11A. Irrigant inflow (hatched in the drawing) occurs in a region 175 having a crescent shape below and partially surrounding the fiber end element 155 as it is positioned as described above. Irrigant outflow (not hatched in the drawing) is primarily directed through the region 176 above the fiber end element 155.

In FIG. 12A, the embodiment of FIG. 8 is illustrated in cross-section. In this embodiment, the external cannula 180 has nearly equal radii at the top surface 180A and the bottom surface 180B. The internal structure includes a first tube 181 having a top arcuate surface 181A and a bottom arcuate surface 181B with essentially flat walls in between. The tube 181 is adapted to receive the telescope 154 and the fiber end element 155. Thus the radius of the bottom arcuate surface 181B matches the radius of the end element 155. Likewise, the radius of the top arcuate surface 181A matches the radius of the telescope 154. An irrigant inflow channel is provided by bonding the element 182 to the sidewalls of the tube at 181 to form a crescent shaped opening. The radius of the element 182 is slightly smaller than the radius of the bottom surface 180B of the external cannula. Although not shown, a spacer, as described above in FIG. 8 is bonded to the top of the arcuate surface 181A to securely position the inner structure within the external cannula 180. FIG. 12B illustrates the flow of irrigant for the embodiment illustrated in FIG. 12A. Irrigant inflow (hatched in the drawing) occurs in a region 185 having a crescent shape below and partially surrounding the fiber end element 155 as it is positioned as described above. Irrigant outflow (not hatched in the drawing) is primarily directed through the region 186 above the fiber end element. Additional irrigant outflow occurs in regions 187, 188, 189, and 190.

In all three embodiments, a crescent shaped irrigant inflow path (for irrigant flowing into the working region) below and partially surrounding the fiber end element 155, is established by the internal structure of the endoscope. In addition, the fiber end element 155 is positioned in a manner that limits lateral movement and maintains a fixed distance (corresponding to the distance D of FIG. 8) between the outside wall on which the emission surface of the fiber end element 155 is found, and the lower arcuate surface (150B, 170B or 180B) of the external cannula.

Figure 13:
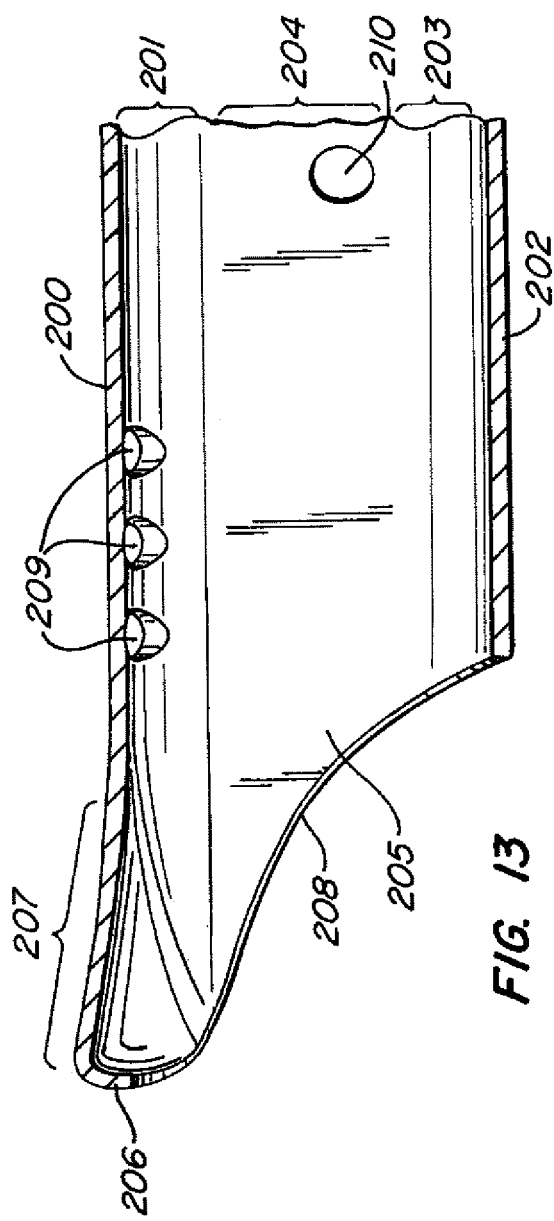
FIG. 13 is a side cross-sectional view of the distal end of the external cannula in one embodiment.

FIG. 13 shows a cross-section of the distal end of the external cannula for the embodiment of FIG. 12A. The external cannula has a top wall 200 that is essentially straight along the major axis of the cannula, and is arcuate in the region 201, as described with reference to FIG. 12A. The external cannula has a lower wall 202, that is essentially parallel to the top wall 200, and is arcuate in the region 203, as described referenced FIG. 12A. In the region 204, the far side wall 205 of the external cannula is essentially straight. The distal end face 206 is formed on a hood structure 207, which flares slightly outwardly from the essentially straight top wall 200, and has a blunt rounded end. The distal end 208 of the external cannula at the lower wall 202, the side wall 204 and lower arcuate region 203 is curved inwardly toward the proximal end of the cannula to establish the hooded area for the working region as described above. Irrigant outflow ports 209 are formed in the top arcuate region 201 to capture any irrigant that escapes outside the external cannula. Likewise, irrigant outflow port 210 is formed in the side wall 205.

Figure 14:
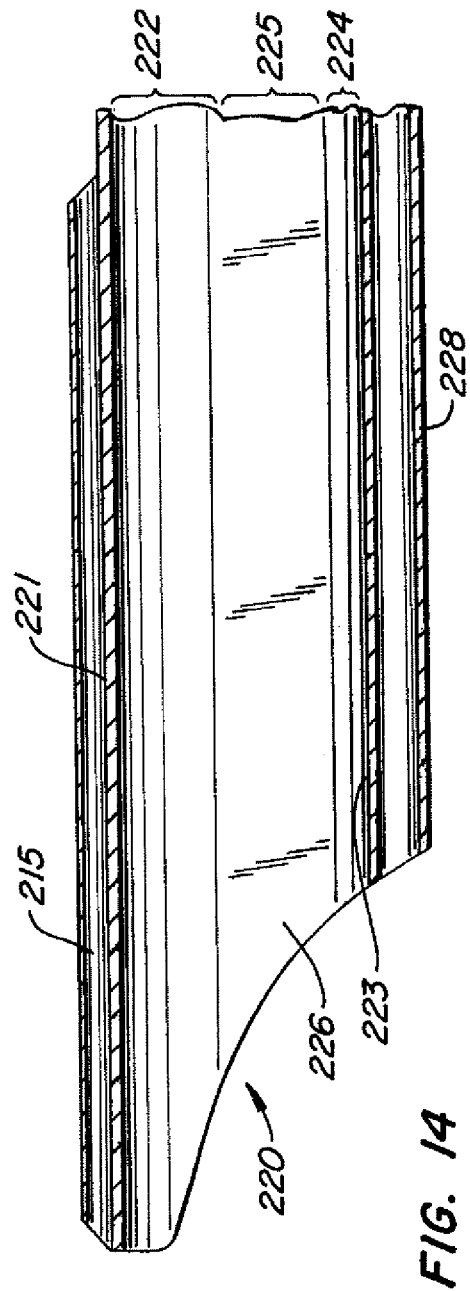
FIG. 14 is a side cross-sectional view of the distal end of the internal structures adapted for use with the external cannula shown in FIG. 13.

FIG. 14 shows a cross-section of the distal end of the internal cannula for the embodiment of FIG. 12A. The internal cannula structure has a spacer formed by tube 215 with beveled front and rear surfaces, bonded to the top wall 221 of the tube 220. Tube 220 is adapted to receive the telescope and the fiber end element. The top wall 221 of the tube 220 is essentially straight, and coupled to the top arcuate portion 222, that is adapted to fit the radius of the telescope. The tube 220 has a bottom wall 223 which is essentially parallel to the top wall 221 and coupled to the bottom arcuate portion 224 which is adapted to fit the a radius of the fiber end element. The far wall 226 of the tube at 220 is essentially flat between the arcuate portions 222, 224. The irrigant inflow tube is defined by wall 228, which is essentially parallel to the bottom wall 223 of the tube 220. The internal cannula structure of FIG. 14 fits slidably within the exterior cannula structure of FIG. 13. The combination of the thickness of the bottom wall 202 of the external cannula, and the thickness of the irrigant inflow channel defined by wall 228 and wall 223 of the internal structure establish the distance D at which the fiber end element is maintained away from tissue in the target region.

Figure 15:
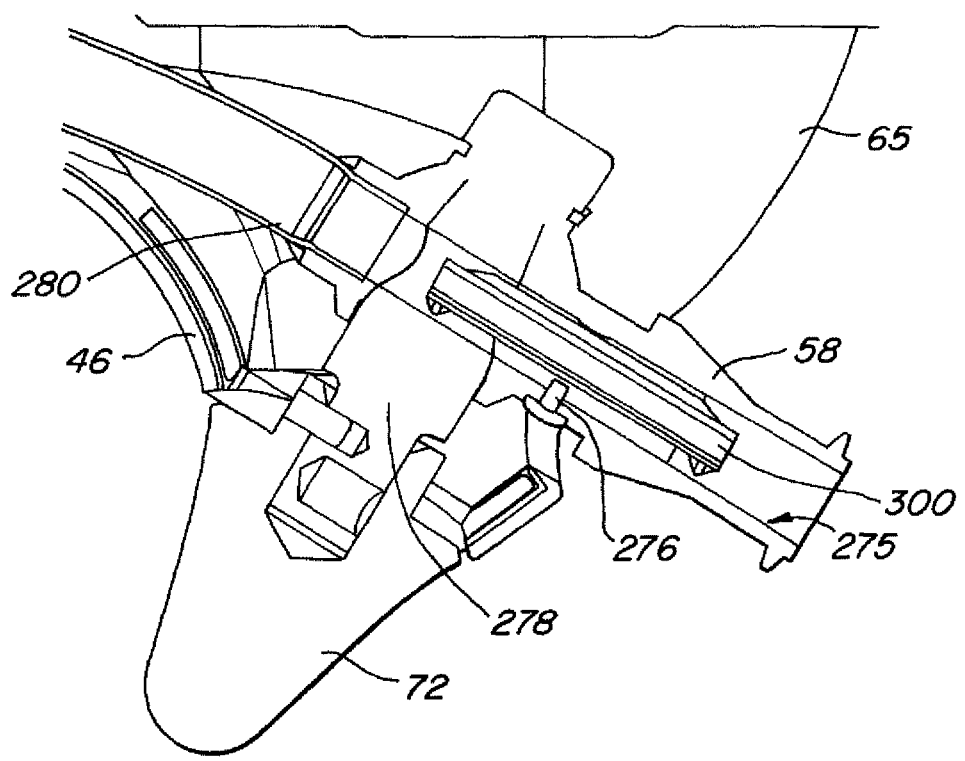
FIG. 15 illustrates cooperation of a travel limiter and a pin within a fiber lumen on the endoscope.

FIG. 15 illustrates the proximal end of the lumen in the endoscope adapted received the fiber and cooperate with the travel limiter 300, which is shown apart from the fiber in the drawing. A fitting 58 defines a lumen 275 into which the fiber is received with the travel limiter 300 bonded thereto. The fitting 58 includes a cylindrical inner lumen coupled to a stopcock valve 278 which is opened to receive the fiber, and provide a continuous lumen 275 having a cylindrical bearing surface within which the travel limiter 300 is able to move. On the distal side of the stopcock valve 278, a tube 280 is bonded which directs the fiber into the internal structure of the endoscope as described above. As shown in FIG. 15, the cover 65 includes an extension 46 surrounding the stopcock valve 278 and the tube 280, while the fitting 58 extends outwardly. A pin 276 or other stop element extends into the lumen 275 and cooperates with the travel limiter 300 to prevent rotation beyond a predefined arc of the fiber.

Figure 16:
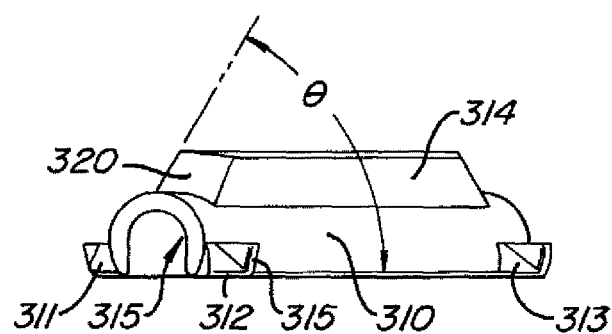
FIG. 16 illustrates the structure of a travel limiter for use with a fiber adapted for the endoscope described herein.

The structure of the travel limiter 300 (in the form of a cam in this embodiment) is illustrated in FIG. 16. The travel limiter includes a cylindrical fiber sheath body 310 adapted to fit over the sheath of the optical fiber and be bonded thereto. Appendages 311, 312, 313 are formed on the body 310 with arcuate outside surfaces (e.g. surface 315 on appendage 312), which are adapted to center the fiber, and to slide rotationally and longitudinally on the bearing surface within the lumen 275. A ridge 314 extends along the major axis of the body 310 having sidewalls with a rear beveled surface 320 (and a front beveled surface) set at an angle theta, such as about 60°. The sidewalls are positioned so that in cooperation with the pin 276, rotational movement of the fiber is limited to a predefined arc. The width of the ridge 314 between the side walls determines the range of rotational movement of the fiber.

Although not shown in FIG. 15, seal 70 (See, FIG. 1 and FIG. 1A) when attached to the fitting 58 acts to prevent longitudinal motion of the travel limiter 300 in a direction away from the distal end of the endoscope. Longitudinal motion in a direction toward the distal end of the endoscope is not actively limited in this embodiment, but is controlled by the surgeon by observing the fiber end element within the field of view of the telescope, in cooperation with feel of limited movement defined by the length of the bearing surface in lumen 275. In an alternative embodiment, a structure may be added to rigidly limit longitudinal motion toward the distal end. The length of the ridge 314 is selected so that when the fiber is fully withdrawn against the seal 70, the ridge remains in a position to cooperate with the pin 276, thereby providing for control of rotational motion of the fiber over a predefined length of longitudinal motion which is the equal to about twice the length of the ridge 314.

Figure 17:
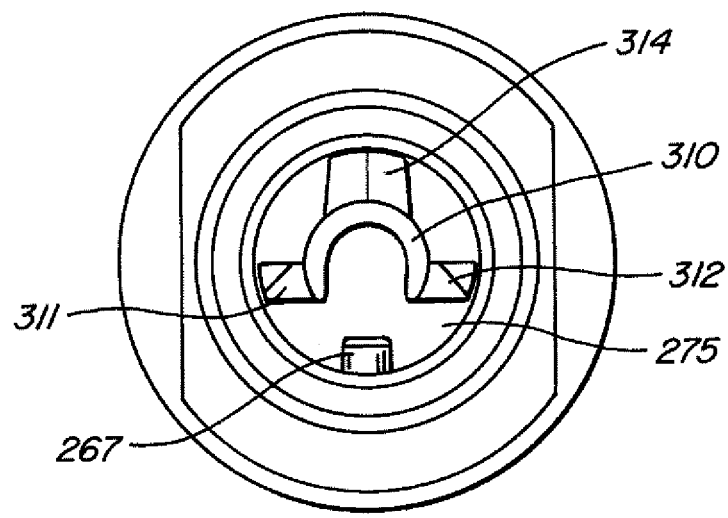
FIG. 17 is an end view of the fiber lumen with a travel limiter cam positioned inside in a vertical position

FIG. 17 illustrates positioning of the travel limiter 300 from an end of view within the lumen 275. Appendages 311 and 312 and the ridge 314 are adapted to secure the body 310 at a position that is substantially centered within the lumen 275, and so that as the fiber is rotated, it remains positioned near the center and does not contact the pin 267.

Figure 18:
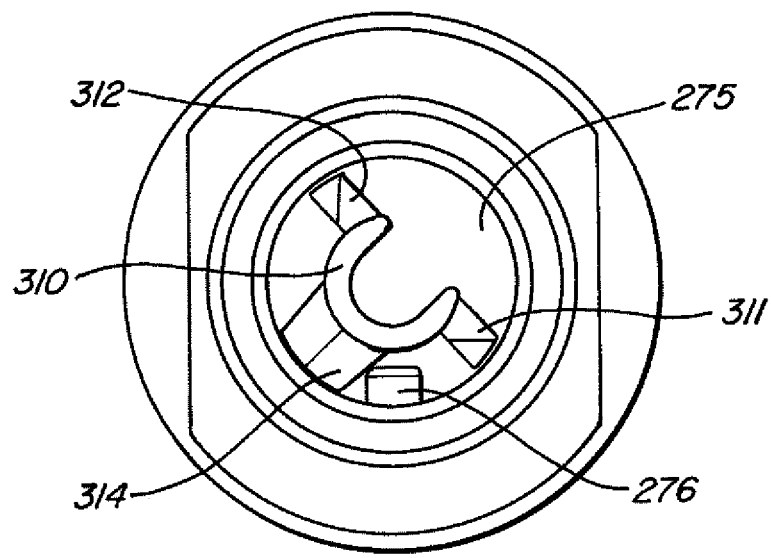
FIG. 18 is an end view of the fiber lumen with a travel limiter cam positioned in a rotated position.

As illustrated in FIG. 18, when the fiber is rotated in a counterclockwise direction, the ridge 314 eventually contacts the pin 276 to limit the rotational motion. The ridge 314 cooperates in a similar manner with the pin 276 to limit clockwise motion. In illustrated embodiment, the travel limiter will allow rotational motion of about 270°, with the remaining 90° of the circle being blocked to prevent irradiation of the hood structure on the distal end of the endoscope.

Figure 19:
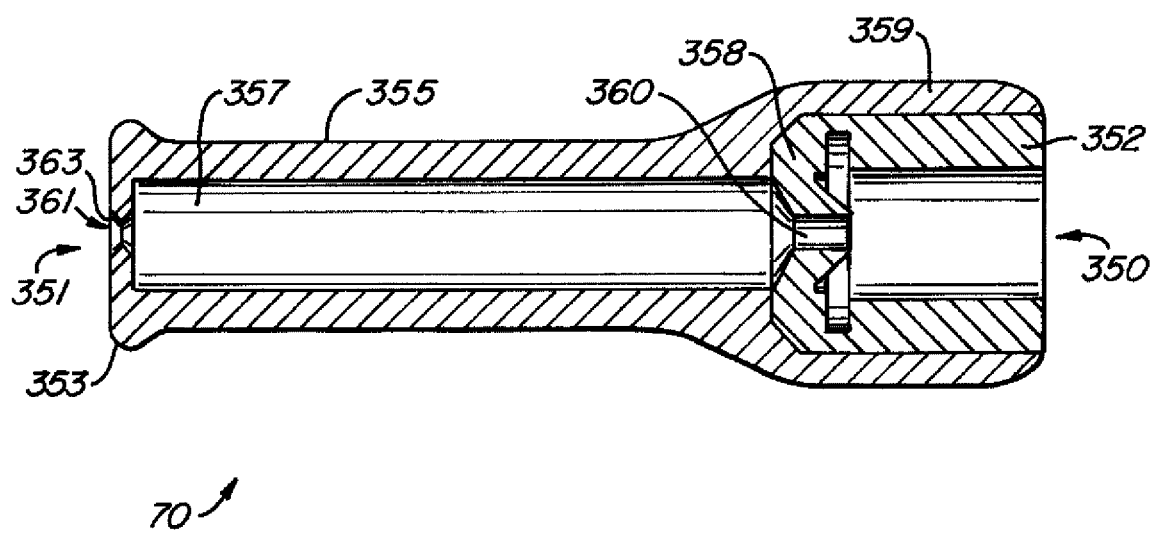
FIG. 19 is a cross-sectional view of an embodiment of a fiber port cap for sealing a fiber port on an endoscope as described herein, adapted to be placed on a optical fiber like that of FIG. 1A.

FIG. 19 is a cross-section view of the fiber port cap 70 shown in FIG. 1A, adapted to at least partially close the fiber port while admitting the fiber into the port and allowing rotational and translational movement of the fiber. The fiber port cap 70 has a distal end 350 adapted to fit over the port 279 shown in FIG. 15, and a proximal and 351 adapted to receive the fiber. The embodiment illustrated includes a first portion 352 and a second portion 353. The first portion 352 comprises a cylindrical body essentially open on the distal end 350 to fit over the outside of the port 279 a granular slot reader 56 adapted to fit over the ridge at the outer edge of the port 279, and a conical portrait grip 358 which extends on the proximal end of the element 352 inwardly. The conical portrait grip 358 includes a passage 360 adapted to receive the optical fiber. The element 353 has a relatively elongated cylindrical body 355 with an interior 357 substantially greater in diameter than the fiber. An enlarged cylindrical portion 359 adapted to fit on the outside surface of the element 352 is included. An interface between element 352 and the enlarged portion 359 is bonded securely. The proximal end of the element 353 has a circular opening 361 with tapered edge 363 adapted to snugly engage the fiber. In a representative embodiment the element 352 is formed using a relatively low durometer silicone rubber. The element 353 is formed using a medium durometer silicone rubber. Together, they provide a fiber port cap that is flexible enough to be installed and removed from the endoscope, and provides a firm enough seal to allow movement of the fiber during use and prevent leakage of irrigant. The seal provided prevents back flow of irrigant from within the endoscope during operation of the device. Also, the conical port grip element 358 acts as a stop for the travel limiter 300 illustrated in FIG. 15.

An endoscope for laser surgery that has a channel to guide a laser fiber to an operating field has been described characterized by various combinations of the following features:
  a. The endoscope is adapted for use with an operating field being a body cavity to interior cavity of an organ filled with an aqueous irrigation fluid.
  b. The endoscope having a build in telescope for visualization of the operating field.
  c. The endoscope having a separate channel to guide irrigation fluid to the operating field.
  d. The endoscope having a separate channel to guide irrigation fluid and tissue particles out of the operating field.
  e. The channel guiding the laser fiber giving the fiber very good stability and allowing the surgeon to control the position of the laser fiber relative to the tissue face.
  f. The channel guiding the irrigation fluid out of the body cavity in a way that vapor bubbles and tissue particles are flowing outside the visual field of the telescope.
  g. The channel guiding the irrigation fluid to the operating field in such a way that irrigation fluid is directed predominantly towards the spot where the laser beam hits the tissue.
  h. The channel guiding the irrigation fluid to the operating field guiding the fluid in such a way that vapor bubbles and tissue particles created by the laser tissue interaction are carried away out of the field of view of the surgeon.
  i. Channels to guide laser fiber and irrigation fluid to the operating field located in a way that irrigation fluid flows predominantly between a "hot" emission face of laser fiber and target tissue.
  j. A component of the endoscope that interfaces with a device attached to laser fiber that prevents the surgeon from aiming laser beam on components of endoscope.
    i. Such device limiting rotation of laser fiber in the channel guiding the laser fiber to the operating field in such a way to prevent the laser beam from being aimed at the protruding tip of endoscope.

ii. Such device limiting translation of fiber inside the channel guiding the laser fiber to the operating field in such a way to prevent the laser beam from being aimed at an endoscope component.

iii. Such device allowing translation and rotation of the laser fiber inside the channel guiding the laser fiber to the operating field in such a way to allow the laser beam to be aimed in all directions where the laser beam does not hit an endoscope component.

iv. Such device allowing translation and rotation of laser fiber inside the channel guiding the laser fiber to the operating field in such a way that the laser beam can be aimed at targets outside the field of view of the telescope.

v. A travel limiting mechanism, including for example a pin protruding into the channel guiding the laser fiber that interfaces with a fin or cam mounted on the laser fiber. The fin oriented in a way that the laser beam being emitted sideways out of the laser fiber does not fire in the direction of a distal tip of the endoscope that is protruding beyond the end of the channel guiding the laser fiber.

vi. An aperture having a flexible or resilient seal on the channel that is guiding the laser fiber with the aperture interfacing with a device on the laser fiber in such way that user feels resistance when device pushes against aperture.

An optical fiber assembly is described including adapted for use with endoscopes as described herein is also described, including a fiber end element adapted to direct laser energy into a working region on tissue, a travel limiter adapted to cooperate with a fiber port to limit longitudinal and rotational movement of the fiber, fiber port cap adapted to couple the fiber to the fiber port, while providing a seal and allowing for movement of the fiber, a handle adapted for use by a surgeon to facilitate movement of the fiber during use, and a fiber coupler, adapted to couple the fiber to a source of laser energy.

One embodiment of an endoscope comprises a continuous flow laser cystoscope comprised of inner and outer sheaths defining cannulas. The inner sheath having plural channels to guide a telescope, a laser fiber and irrigation fluid to the operating filed. Space between inner and outer sheath serving as pathway to guide irrigation fluid out of the operating field. The laser fiber being located underneath the telescope in the direction of tissue. A channel or pathway that guides irrigation fluid to the operating field being located between laser fiber and tissue. A channel or pathway that guides irrigation fluid out of the body cavity being located on top of the telescope. A channel that guides the laser fiber having an inner diameter only slightly larger than the outer diameter of laser fiber near the tip. A "channel" or "pathway" can comprise two or more tubes of different diameter that sit within each other or are otherwise arranged to cooperate as a pathway or channel.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. An endoscope for insertion within a body lumen, comprising:

an external cannula having a proximal end and a distal end, and a plurality of tubes within the external cannula, the plurality of tubes having ends at or near the distal end of the external cannula and being adapted for receiving a telescope and for receiving an optical fiber having a side firing tip, and for providing for inflow and outflow of an irrigant, the distal end of the external cannula having a bottom side and a top side, with an opening facing the bottom side defining a working region within the body lumen;

a telescope having a field of view directed laterally into the working region at or near the distal end;

an optical fiber having a side firing tip, the side firing tip having an emission surface through which radiation from the optical fiber is directed laterally;

a guide element at or near the distal end of the external cannula, adapted to moveably support the optical fiber in a position spaced away from the inner wall of the external cannula, and limit lateral movement of the side firing tip without preventing longitudinal movement of the side firing tip within the working region, and without preventing rotational movement of the side firing tip over at least a predetermined arc; and an irrigant nozzle element at the end of one of the plurality of tubes at or near the distal end of the external cannula, the irrigant nozzle element comprising an irrigant inflow channel located on a side of the optical fiber having the emission surface and an irrigant outflow channel on a side of the optical fiber opposite the emission surface, wherein, during use, inflowing irrigant is directed over the emission surface of the side firing tip and into the working region as the side firing tip is moved over said predetermined distance and said predetermined arc within the working region and then the irrigant is drawn into the irrigation outflow channel for removal from the working region.

2. The endoscope of claim 1, wherein said side firing tip has a bearing surface, and the guide element comprises a stationary bearing having an arcuate surface mating with the bearing surface of the side firing tip.

3. The endoscope of claim 1, wherein the side firing tip comprises a cylindrical cap coupled to the optical fiber, the cylindrical cap having a bearing surface, and the guide element comprises a stationary bearing having an arcuate surface mating with the bearing surface of the cylindrical cap.

4. The endoscope of claim 1, wherein the plurality of tubes includes a first tube adapted to receive the telescope and the optical fiber, and wherein said side firing tip has a bearing surface, and the guide element comprises an arcuate inside surface of said first tube mating with the bearing surface of the side firing tip, and wherein said telescope cooperates with the arcuate inside surface to limit lateral movement of side firing tip.

5. The endoscope of claim 1, wherein the irrigant nozzle comprises a stationary ending element of a second tube in the plurality of tubes between the guide element for the side firing tip and the bottom side of the external cannula, the ending element defining an opening having a crescent-like shape, the crescent-like shape partially surrounding the side firing tip to direct the irrigant over the emission face as the side firing tip is moved over said predetermined distance and said predetermined arc.

6. The endoscope of claim 1, wherein the plurality of tubes includes a first tube adapted to receive the optical fiber, and wherein the irrigant nozzle comprises an ending element coupled to a second tube in the plurality of tubes between the guide element for the side firing tip and the bottom side of the external cannula, the ending element defining an opening having a crescent-like shape, the crescent-like shape partially surrounding the side firing tip to direct the irrigant over the emission face as the side firing tip is moved over said predetermined distance and said predetermined arc.

7. The endoscope of claim 1, including a plurality of ports at the proximal end of the external cannula, including a fiber port adapted to receive the optical fiber, and having a travel limiter element, and
   a travel limiter coupled to the optical fiber which cooperates with the travel limiter element in the fiber port to limit the rotational movement of the optical fiber over the predetermined arc, thereby preventing rotation of the emission surface of the side firing tip into a position that does not face the opening in the bottom side of the distal end.

8. The endoscope of claim 1, including a plurality of tube ports at the proximal end of the external cannula, including a fiber port adapted to receive the optical fiber, the fiber port having an opening with a stop element, and
   a travel limiter coupled to the optical fiber which cooperates with the stop element in the fiber port to limit the longitudinal movement of the optical fiber in a direction away from the distal end of the external cannula.

9. The endoscope of claim 1, including an irrigant backflow port at or near the distal end of the external cannula, and between the guide element and the top side of the external cannula.

10. The endoscope of claim 1, wherein the guide element positions the optical fiber between the telescope and the irrigant nozzle, and including an irrigant backflow port at or near the distal end of the external cannula, and between the telescope and the top side of the external cannula adapted to draw the irrigant from the irrigant nozzle across the field of view of the telescope and across the emission surface of the side firing tip.

11. The endoscope of claim 1, wherein during delivery of radiation, irrigant exits the irrigant inflow channel, flows across the emission surface of the optical fiber and then enters the irrigant outflow channel.

12. An endoscope for insertion within a body lumen, comprising:
   an external cannula having a proximal end and a distal end, and a plurality of tubes within the external cannula, the plurality of tubes having ends at or near the distal end of the external cannula and being adapted for receiving a telescope, for receiving an optical fiber having a tip with a radiation emission surface, and for providing for inflow and outflow of an irrigant, the distal end of the external cannula having a top side and a bottom side, with an opening facing the bottom side defining a working region within the body lumen;
   a telescope having a field of view directed laterally into the working region at or near the distal end;
   an optical fiber with a side firing tip having an emission surface through which radiation from the optical fiber is directed laterally;
   a guide element at or near the distal end of the external cannula, adapted to moveably support the optical fiber for movement within a working region;
   an irrigant inflow channel located on a side of the optical fiber having the emission surface; and
   an irrigant outflow channel on a side of the optical fiber opposite the emission surface,
   wherein, during use, inflowing irrigant is directed over the emission surface of the side firing tip as the tip is moved within the working region, and
   wherein after the inflowing irrigant is delivered over the emission surface and into the working region, the irrigant is drawn into the irrigant outflow channel for removal from the working region.

13. The endoscope of claim 12, wherein the irrigant nozzle comprises a stationary ending element of a second tube in the plurality of tubes between the guide element for the tip and the bottom side of the external cannula, the ending element defining an opening having a crescent-like shape, the crescent-like shape partially surrounding the tip to direct the irrigant over the emission face as the tip is moved over a predetermined distance and a predetermined arc.

14. The endoscope of claim 12, wherein the plurality of tubes includes a first tube adapted to receive the optical fiber, and wherein the irrigant nozzle comprises an ending element coupled to a second tube in the plurality of tubes between the guide element for the tip and the bottom side of the external cannula, the ending element defining an opening having a crescent-like shape, the crescent-like shape partially surrounding the tip to direct the irrigant over the emission face as the side firing tip is moved over a predetermined distance and a predetermined arc.

15. The endoscope of claim 12, wherein the irrigant nozzle is positioned between the tip and the bottom side of the external cannula, and including an outflow channel within the external cannula which is arranged to draw the irrigant from the irrigant nozzle toward the top side of the external cannula across the tip.

16. An endoscope for insertion within a body lumen, comprising:
   an external cannula having a proximal end and a distal end, and a plurality of tubes within the external cannula, the plurality of tubes having ends at or near the distal end of the external cannula and being adapted for receiving a telescope and for receiving an optical fiber, the distal end of the external cannula having a bottom side and a top side, with an opening facing the bottom side defining a working region within the body lumen;
   a telescope having a field of view directed laterally into the working region at or near the distal end;
   the optical fiber having a side firing tip, the side firing tip having an emission surface through which radiation from the optical fiber is directed into the working region;
   a guide element at or near the distal end of the external cannula, adapted to moveably support the optical fiber in a position spaced away from the inner wall of the external cannula, and limit lateral movement of the optical fiber tip;
   a plurality of ports at the proximal end of the external cannula, including a fiber port adapted to receive the optical fiber;
   the fiber port having a travel limiter element and an opening with a longitudinal stop element;
   a travel limiter coupled to the optical fiber which cooperates with the travel limiter element to limit the rotational movement of the optical fiber over a predetermined arc, thereby preventing rotation of the emission surface of the tip into a position that does not face the opening in the bottom side of the distal end;
   the travel limiter cooperating with the longitudinal stop element to limit the longitudinal movement of the optical fiber in a direction away from the distal end of the external cannula; and
   an irrigant nozzle element at the end of one of the plurality of tubes at or near the distal end of the external cannula, the irrigant nozzle element comprising an irrigant inflow channel located on a side of the optical fiber having the emission surface and an irrigant outflow channel on a side of the optical fiber opposite the emission surface, wherein, during use, inflowing irrigant is directed over the emission surface of the side firing tip as the tip is moved within the working region and then drawn into the irrigant outflow channel for removal from the working region.

17. The endoscope of claim 16, wherein during delivery of radiation, irrigant exits the irrigant inflow channel, flows across the emission surface of the optical fiber and then enters the irrigant outflow channel.

18. An endoscope for insertion within a body lumen, comprising:

an external cannula having a proximal end and a distal end, and a plurality of tubes within the external cannula, the plurality of tubes having ends at or near the distal end of the external cannula and being adapted for receiving a telescope and for receiving an optical fiber having a side firing tip, and for providing for inflow and outflow of an irrigant, the distal end of the external cannula having a bottom side and a top side, with an opening facing the bottom side defining a working region within the body lumen;

a telescope having a field of view directed laterally into the working region at or near the distal end;

an optical fiber having a side firing tip, the side firing tip having an emission surface through which radiation from the optical fiber is directed laterally; and an irrigant nozzle element at the end of one of the plurality of tubes at or near the distal end of the external cannula, the irrigant nozzle element comprising an irrigant inflow channel located on a side of the optical fiber having the emission surface and an irrigant outflow channel on a side of the optical fiber opposite the emission surface, wherein, in use, inflowing irrigant is directed over the emission surface of the side firing tip and into the working region as the side firing tip is moved over said predetermined distance and said predetermined arc within the working region and then the irrigant is drawn into the irrigation outflow channel.

19. The endoscope of claim 18, further comprising a plurality of ports at the proximal end of the external cannula, including a fiber port adapted to receive the optical fiber, and having a travel limiter element, and a travel limiter coupled to the optical fiber which cooperates with the travel limiter element in the fiber port to limit the rotational movement of the optical fiber over the predetermined arc, thereby preventing rotation of the emission surface of the side firing tip into a position that does not face the opening in the bottom side of the distal end.

20. The endoscope of claim 18, further comprising a plurality of tube ports at the proximal end of the external cannula, including a fiber port adapted to receive the optical fiber, the fiber port having an opening with a stop element, and a travel limiter coupled to the optical fiber which cooperates with the stop element in the fiber port to limit the longitudinal movement of the optical fiber in a direction away from the distal end of the external cannula.

21. The endoscope of claim 18, further comprising an irrigant backflow port at or near the distal end of the external cannula.

* * * * *